(12) United States Patent
Manolidis (10) Patent No.: US 11,666,464 B2
(45) Date of Patent: Jun. 6, 2023

(54) MAGNETIC STENT AND STENT DELIVERY

(71) Applicant: Spiros Manolidis, Southlake, TX (US)

(72) Inventor: Spiros Manolidis, Southlake, TX (US)

(73) Assignee: Tensor Flow Ventures LLC, Dallas, TX (US)

( * ) Notice: Subject to any disclaimer, the term of this patent is extended or adjusted under 35 U.S.C. 154(b) by 0 days.

(21) Appl. No.: 16/752,315

(22) Filed: Jan. 24, 2020

(65) Prior Publication Data

US 2020/0237534 A1 Jul. 30, 2020

Related U.S. Application Data

(63) Continuation-in-part of application No. 16/752,265, filed on Jan. 24, 2020, and a continuation-in-part of application No. 16/752,343, filed on Jan. 24, 2020.

(60) Provisional application No. 62/797,933, filed on Jan. 28, 2019, provisional application No. 62/797,932, filed on Jan. 28, 2019, provisional application No. 62/797,944, filed on Jan. 28, 2019.

(51) Int. Cl.
| | |
|---|---|
| *A61F 2/95* | (2013.01) |
| *A61F 2/848* | (2013.01) |
| *A61B 5/00* | (2006.01) |
| *A61B 5/026* | (2006.01) |

(52) U.S. Cl.
CPC ............. *A61F 2/848* (2013.01); *A61B 5/026* (2013.01); *A61B 5/6862* (2013.01); *A61F 2/95* (2013.01); *A61F 2210/009* (2013.01); *A61F 2220/0008* (2013.01)

(58) Field of Classification Search
CPC .... A61F 2/848; A61F 2/95; A61F 2220/0008; A61F 2210/009; A61F 2/064; A61B 5/6862; A61B 5/026; A61B 5/0205
See application file for complete search history.

(56) References Cited

U.S. PATENT DOCUMENTS

| | | |
|---|---|---|
| 4,054,128 A | 10/1977 | Seufert et al. |
| 4,873,965 A | 10/1989 | Danieli |

(Continued)

FOREIGN PATENT DOCUMENTS

| | | |
|---|---|---|
| CN | 104116484 A1 | 10/2014 |
| DE | 102016007669 A1 | 12/2017 |

(Continued)

OTHER PUBLICATIONS

International Preliminary Report on Patentability for International Application No. PCT/US2020/015447 dated Feb. 17, 2021.

(Continued)

*Primary Examiner* — Suzette J Gherbi
(74) *Attorney, Agent, or Firm* — David W. Carstens; J. Andrew Reed; Carstens, Allen & Gourley, LLP (57) ABSTRACT

A stent apparatus for use in surgical applications having a hollow tubular section with a proximal end and a distal end. Additionally, the stent apparatus can have at least one anchor point connected to the hollow tubular section. The hollow tubular section may also have a modifiable member, and a magnetic connection node. The stent may also be wrapped in a material that has magnetic properties. The delivery of the stent can include a stent delivery tool for inserting a stent into a vessel.

20 Claims, 7 Drawing Sheets

(56) References Cited

U.S. PATENT DOCUMENTS

| | | | |
|---|---|---|---|
| 5,141,516 A * | 8/1992 | Detweiler | A61B 17/11 606/154 |
| 5,349,133 A | 9/1994 | Rogers | |
| 5,492,131 A | 2/1996 | Galel | |
| 5,507,725 A | 4/1996 | Savage et al. | |
| 5,536,236 A | 7/1996 | Fab et al. | |
| 5,562,641 A | 10/1996 | Flomenblit et al. | |
| 5,573,493 A | 11/1996 | Sauer et al. | |
| 5,733,325 A | 3/1998 | Robinson et al. | |
| 5,851,218 A | 12/1998 | Lev | |
| 6,270,524 B1 | 8/2001 | Kim | |
| 6,361,559 B1 * | 3/2002 | Houser | A61B 17/11 623/1.36 |
| 6,485,513 B1 | 11/2002 | Fan | |
| 6,517,574 B1 | 2/2003 | Chuter | |
| 6,565,581 B1 | 5/2003 | Spence et al. | |
| 6,699,263 B2 | 3/2004 | Cope | |
| 6,899,672 B2 | 5/2005 | Chin et al. | |
| 7,090,637 B2 | 8/2006 | Danitz et al. | |
| 7,476,256 B2 | 1/2009 | Meade et al. | |
| 7,678,068 B2 | 3/2010 | Levine et al. | |
| 7,766,962 B1 | 8/2010 | Quinn | |
| 8,097,009 B2 * | 1/2012 | Wu | A61F 2/06 606/155 |
| 8,211,025 B2 | 7/2012 | Donaldson et al. | |
| 8,298,161 B2 | 10/2012 | Vargas | |
| 8,360,968 B2 | 1/2013 | Hadani | |
| 8,444,549 B2 | 5/2013 | Viola et al. | |
| 8,512,232 B2 | 8/2013 | Rothberg et al. | |
| 8,615,288 B2 | 12/2013 | Govari et al. | |
| 9,220,568 B2 | 12/2015 | Bromander et al. | |
| 9,326,870 B2 | 5/2016 | Berglund et al. | |
| 9,757,856 B2 | 9/2017 | Oyola et al. | |
| 9,820,746 B2 | 11/2017 | Imran | |
| 9,949,692 B2 * | 4/2018 | Hunter | A61B 5/01 |
| 10,420,661 B2 | 9/2019 | Hodgkinson et al. | |
| 10,542,931 B2 | 1/2020 | Kuraguntla et al. | |
| 11,033,377 B2 * | 6/2021 | Houston | A61F 2/915 |
| 11,491,003 B2 | 11/2022 | Arbefeuille et al. | |
| 11,596,408 B2 | 3/2023 | Lukin et al. | |
| 2001/0004696 A1 | 6/2001 | Roberts et al. | |
| 2002/0099405 A1 | 7/2002 | Yurek et al. | |
| 2002/0143347 A1 * | 10/2002 | Cole | A61B 17/11 606/153 |
| 2003/0135266 A1 | 7/2003 | Chew et al. | |
| 2003/0216801 A1 * | 11/2003 | Tweden | A61F 2/2493 623/1.13 |
| 2004/0116999 A1 | 6/2004 | Ledergerber | |
| 2004/0167604 A1 | 8/2004 | Stinson | |
| 2005/0154444 A1 * | 7/2005 | Quadri | A61F 2/07 623/1.13 |
| 2005/0154448 A1 | 7/2005 | Cully et al. | |
| 2006/0052736 A1 | 3/2006 | Tweden et al. | |
| 2006/0074478 A1 | 4/2006 | Feller | |
| 2006/0149349 A1 | 7/2006 | Garbe | |
| 2007/0067014 A1 * | 3/2007 | Ke | A61F 2/07 623/1.13 |
| 2007/0142711 A1 | 6/2007 | Bayer et al. | |
| 2008/0132906 A1 | 6/2008 | Rasmussen | |
| 2008/0255653 A1 | 10/2008 | Schkolnik | |
| 2009/0023998 A1 | 1/2009 | Ratnakar | |
| 2009/0171437 A1 | 7/2009 | Brocker et al. | |
| 2009/0281557 A1 | 11/2009 | Sander et al. | |
| 2009/0287293 A1 * | 11/2009 | Mailhot, Jr. | A61F 2/91 623/1.15 |
| 2010/0030320 A1 | 2/2010 | Feller | |
| 2010/0168835 A1 | 7/2010 | Dorn | |
| 2010/0217082 A1 | 8/2010 | Ito et al. | |
| 2010/0262171 A1 * | 10/2010 | Wu | A61F 2/06 606/151 |
| 2011/0190870 A1 | 8/2011 | Hastings et al. | |
| 2011/0264196 A1 | 10/2011 | Savage et al. | |
| 2012/0071721 A1 | 3/2012 | Remijan et al. | |
| 2012/0123464 A1 | 5/2012 | Rasmussen et al. | |
| 2013/0035751 A1 | 2/2013 | Shalev | |
| 2013/0144380 A1 | 6/2013 | Quadri et al. | |
| 2013/0190741 A1 | 7/2013 | Moll et al. | |
| 2014/0081415 A1 * | 3/2014 | Ruberti | A61B 17/11 264/271.1 |
| 2014/0228936 A1 | 8/2014 | Kassab et al. | |
| 2014/0236064 A1 | 8/2014 | Binmoeller et al. | |
| 2014/0277442 A1 | 9/2014 | Seddon et al. | |
| 2014/0303599 A1 | 10/2014 | Heideman et al. | |
| 2015/0328022 A1 | 11/2015 | Hansen et al. | |
| 2015/0366439 A1 | 12/2015 | Luo et al. | |
| 2016/0120638 A1 | 5/2016 | Michalak | |
| 2016/0242940 A1 | 8/2016 | Krautkremer et al. | |
| 2016/0256610 A1 | 9/2016 | Zhou et al. | |
| 2016/0310077 A1 | 10/2016 | Hunter et al. | |
| 2017/0079785 A1 | 3/2017 | Li | |
| 2017/0086929 A1 | 3/2017 | Moll et al. | |
| 2017/0128072 A1 | 5/2017 | Wang et al. | |
| 2017/0296038 A1 | 10/2017 | Gordon et al. | |
| 2017/0330665 A1 | 11/2017 | Zareei et al. | |
| 2018/0207007 A1 | 7/2018 | Giasolli et al. | |
| 2019/0239879 A1 * | 8/2019 | Zilla | A61B 17/11 |
| 2020/0094398 A1 | 3/2020 | Young et al. | |
| 2020/0237534 A1 | 7/2020 | Manolidis | |
| 2020/0237540 A1 | 7/2020 | Manolidis | |
| 2021/0077247 A1 | 3/2021 | Shalev et al. | |
| 2021/0393424 A1 | 12/2021 | McWeeney et al. | |
| 2022/0273365 A1 * | 9/2022 | Rege | A61L 27/50 |
| 2022/0303150 A1 * | 9/2022 | Jensen | H04L 65/4046 |
| 2023/0026939 A1 | 1/2023 | Manolidis et al. | |
| 2023/0048537 A1 | 2/2023 | Arbefeuille et al. | |

FOREIGN PATENT DOCUMENTS

| | | |
|---|---|---|
| EP | 2063823 A2 | 6/2009 |
| GB | 2452480 A | 11/2009 |
| WO | 0045737 A1 | 8/2000 |
| WO | WO2011116913 A1 | 9/2011 |
| WO | WO18005861 A1 | 1/2018 |
| WO | 2018068106 A1 | 4/2018 |

OTHER PUBLICATIONS

International Search Report and Written Opinion issued by ISA/US dated Jun. 15, 2020 for International Application No. PCT/US2020/015444.

DE102016007669_google_translation.

CN104116484_google_translation.

International Search Report and Written Opinion issued by ISA/US dated Apr. 22, 2020 for International Application No. PCT/US2020/015447.

International Search Report and Written Opinion issued by ISA/US dated Apr. 28, 2020 for International Application No. PCT/US2020/015439.

* cited by examiner

MAGNETIC STENT AND STENT DELIVERY

CROSS-REFERENCE TO RELATED APPLICATION

The present disclosure claims priority to and is a non-provisional conversion of U.S. Provisional Patent Application No. 62/797,933, filed Jan. 28, 2019, and is a continuation-in-part of U.S. patent application Ser. No. 16/752,265, filed Jan. 24, 2020 which claims priority from U.S. Provisional Patent Application No. 62/797,932, filed Jan. 28, 2019, and is a continuation-in-part of U.S. patent application Ser. No. 16/752,343, filed Jan. 24, 2020 which claims priority from U.S. Provisional Patent Application No. 62/797,944, filed Jan. 28, 2019, all of which is incorporated herein by reference in its entirety for all purposes.

BACKGROUND

Technical Field

The present disclosure relates to stents and stent delivery. More particularly, and not by way of limitation, the present disclosure is directed to an apparatus, method, or system for a magnetic stent and magnetic stent delivery.

Description of Related Art

There are many different types of surgeries that can be conducted daily in hospitals across the world. One such surgery is free flap reconstruction. Free flap reconstruction is a well-established method of reconstruction of both soft tissue and bone or composite defects in a wide variety of surgeries. Free flaps are used in order of frequency in head and neck reconstruction, breast reconstruction, orthopedic surgery and a variety of other specialties. Head and neck surgery in particular is a heavy user of free flap reconstruction. This is due to the complexity of defects in a critical area where restoration of functions such as deglutition, phonation, and mastication is of paramount importance in addition to cosmesis.

Free flap reconstruction involves the transfer of tissue from a distant part of the body to the area that needs to be reconstructed. The principle in operation behind this concept is that tissues in the body are supplied in a segmental function. That is that a segment of skin subcutaneous tissue fascia muscle bone or any combination of these can be harvested according to specific location. The transfer of tissue is completed when the free flap vessels (artery and vein) are joined to the donor vessels and then the flap is set into the defect.

Donor vessels are selected from appropriate vessels to match the diameter of the recipient vessels (free flap vessels). In the neck, these are usually branches of the external carotid artery and one of the many veins in the head and neck or the jugular vein itself. Each of the donor vessels are dissected from surrounding tissue, and their edges prepared for anastomosis. In free flap reconstruction, vessels are raised in situ and the vascular supply is dissected out carefully and atraumatically. The vascular supply is then sectioned, preferably at a length of vessel that is appropriate for an anastomosis without tension. This is not always possible as different free flaps have different lengths of vessels according to where they are harvested. For example, free rectus vascular pedicle may have a max length of 8 cm, while radial forearm vascular pedicle may have a max length of 15-20 cm.

Once the vessels are extracted from the appropriate location, the edge preparation begins. The vessel preparation process can take approximately one hour and is performed under optimal conditions with an operating microscope and/or magnifying loops. Considerable skill is required that comes with prolonged surgical training. The anastomoses (joining) themselves are approximately 20 minutes per vessel anastomosis. Venous couplers reduce the amount of time required for venous anastomoses. However, these venous couplers still require suturing for each venous anastomoses, taking considerable time and increasing the time a patient is under anesthesia. There are two general types of anastomoses, an end to end and an end to side. An end-to-end anastomoses is preferred because it is performed rapidly without additional problems and because the vascular dynamics are that of linear flow which gives lesser complication rates. End to end anastomoses account for the majority of vessel joining. However, currently these operations and/or couplings still require significant suturing time, that can lead to other complications. Furthermore, manually suturing vessels, especially in micro vascular surgery is where most of the technical failures occur.

It would be advantageous to have an apparatus, system, or method for a magnetic stent and magnetic stent delivery that overcomes the disadvantages of the prior art. The present disclosure provides such a system and method.

BRIEF SUMMARY

The present invention is directed to a stent and delivery of said stent during open surgery. Thus, in one aspect, the present invention is directed to a stent that may self-modify, or self-expand during or upon delivery or after delivery.

In another aspect, the present invention is directed to a stent that may be delivered with an outer sheath or protective layer. In yet another aspect, the present invention is directed to a stent that may be delivered through a syringe or push release mechanism utilizing magnetic forces.

Therefore, in one aspect, the present invention is directed to a modified self-expanding stent that expands based on magnetic forces. The stent may have anchor points or atraumatic points.

Thus, in one aspect, the present invention is directed to rapidly performing anastomoses without vessel preparation or suturing. In another aspect, the present invention is directed to lengthening the pedicle during grafts and/or distention of the lumen of the vessel during stent operation.

BRIEF DESCRIPTION OF THE DRAWINGS

The novel features believed characteristic of the disclosure are set forth in the appended claims. The disclosure itself, however, as well as a preferred mode of use, further objectives and advantages thereof, will be best understood by reference to the following detailed description of illustrative embodiments when read in conjunction with the accompanying drawings, wherein:

DETAILED DESCRIPTION

An embodiment of the disclosure will now be described.

Figure 1A:
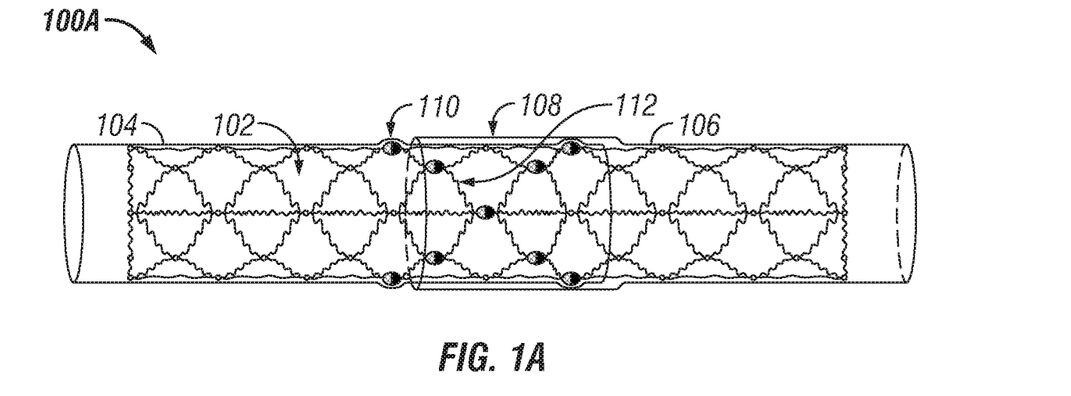
FIG. 1A is an illustration of a magnetic stent coupled to a donor and recipient vessel.

FIG. 1A is an illustration of a magnetic stent 100A coupled to a donor vessel 104 and a recipient vessel 106. While the magnetic stent 100A may also have additional regions, and/or expansion regions the magnetic expansion region 108 allows the magnetic stent 100A to expand in a controlled manner. The stent body 102 can include the magnetic expansion region 108, connection node(s) 110, and/or expandable member(s) 112. In at least one version, the magnetic expansion region 108 is triggered by a magnetic, electric, and/or electromagnetic field. The expansion and/or transition of the magnetic expansion region 108 can also cause the expandable member(s) 112 to transition or expand as well.

Figure 1B:
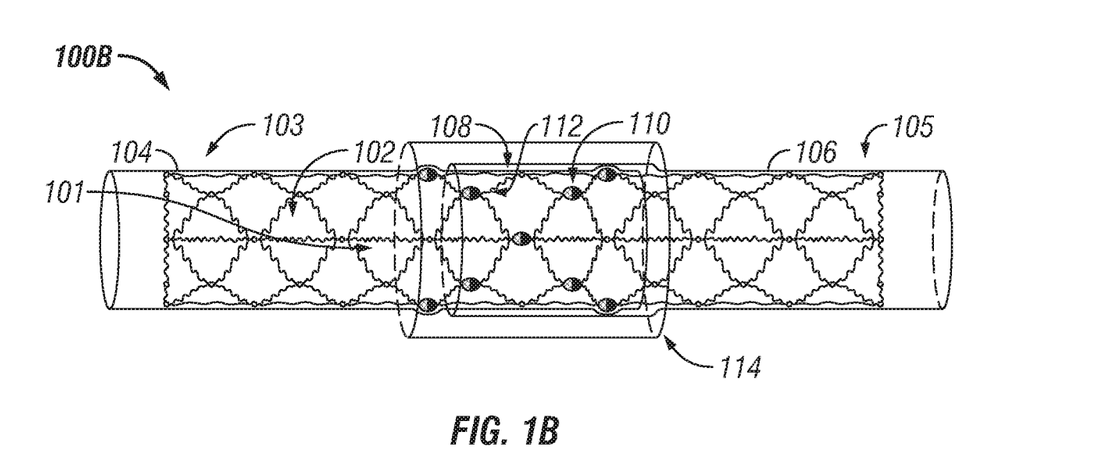
FIG. 1B is an illustration of a magnetic stent with expansion cover coupled to a donor and recipient vessel.

FIG. 1B is an illustration of a magnetic stent 100B coupled to a donor vessel 104 and a recipient vessel 106 and covered with an expansion cover 114. The expansion cover 114 in at least one version provides a magnetic field that prevents and/or activates the expansion of the magnetic stent 100B. In other versions, the expansion cover 114 activates the expansion of a magnetic expansion region of the magnetic stent 100B. The magnetic stent 100B can have a stent body 102 that defines a hollow tubular section 101 having a distal end 103 and proximal end 105. The stent body 102 can also include connection node(s) 110, and/or expandable member(s) 112.

Figure 2:
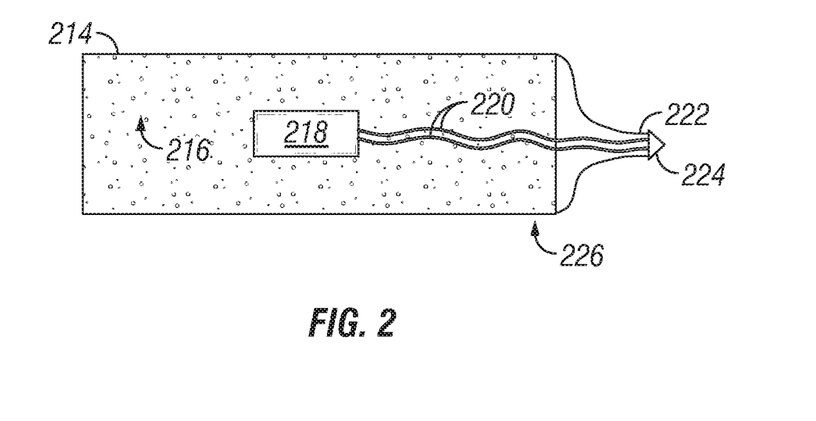
FIG. 2 is an illustration of an expansion cover.

FIG. 2 is an illustration of an expansion cover 214. The expansion cover 214 can contain magnetic material 216, sensor(s) 218, wiring 220, coupling material 222, and/or removal device(s) 224. The cover body 226 can be manufactured and/or formed from fabrics, plastics, alloys, metals, synthetics, and/or combinations thereof. The fabrics, plastics, alloys, metals, synthetics, and/or combinations thereof can be impregnated or contain a magnetic material or magnetic material or elements 216 having magnetic properties that assist in the activation and/or deactivation of the magnetic expansion region. In at least one example, the materials utilized may have an expansion memory property that allows for repeatable changes to the material. The expansion cover 214 may also in at least one version, activate or deactivate additional expansion regions of a stent (not illustrated). The sensor(s) 218, in at least one version would include a blood flow sensor. In other versions, the sensor(s) 218 may also include pulse, blood pressure, temperature, accelerometer, blood glucose, oxygen, airflow, galvanic skin response, electrocardiogram, similar sensors or monitors, or combinations thereof. The wiring 220 can allow the sensor(s) 218 to connect to sensors, monitors, computers, processors, communication devices, transmitters, and/or receivers. The coupling material 222 can allow the expansion cover 214 to be coupled to a removal device 224, and/or secured within, around, and/or near a vessel and/or tissue. The removal device 224 can include a needle, and/or a syringe.

Figure 3A:
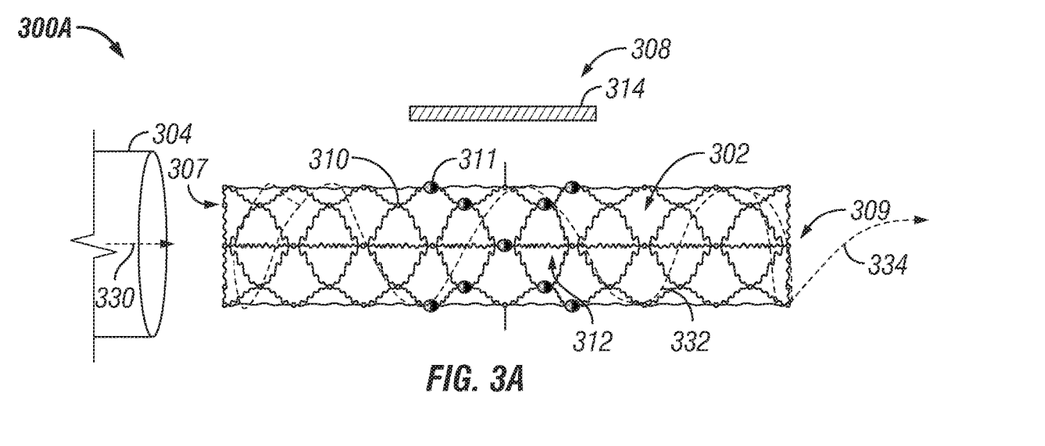
FIG. 3A is an illustration of a magnetic stent and donor vessel.

FIG. 3A is an illustration of a magnetic stent 300A and a donor vessel 304. The magnetic stent 300A can have a stent body 302 that defines the hollow structure (not illustrated) that allows for a fluidic transfer, such as, but not limited to a blood flow 330, from a first opening 307 of the magnetic stent 300A to a second opening 309 of the magnetic stent 300A. In at least one version, the magnetic stent 300A has a magnetic expansion region 308 that can expand, contract, and/or compress based on a magnetic field created by an expansion cover 314. The expansion cover 314 can include magnetic materials and/or elements that can be activated and/or deactivated by sensor(s) or other monitoring devices coupled to the expansion cover 314 via a wired or wireless connection.

Additionally, the stent body 302 can also include connection node(s) 310, magnetic node(s) 311, and/or expandable member(s) 312. The expandable member(s) 312 may be manufactured and/or formed from plastics, silicon, metal, metal alloys, synthetic materials, polymers, absorbable polymers, Teflon, Mylar, carbon fiber, magnetic materials or elements, other like materials, or combinations thereof. In at least one embodiment, the expandable member(s) may also be a modifiable member. The material should have a compressibility that allows for the expandable member(s) 312 to be approximately one-half its normal size, be approximately one-quarter of its normal size, or any other fraction of one whole portion of the expandable member(s) 312. The expandable member(s) 312 may also be formed, constructed, and/or manufactured utilizing a material that may have a memory effect such as a pliable plastic or silicon material, but other materials such as plastics, silicon, metal, metal alloys, synthetic materials, polymers, absorbable polymers, Teflon, Mylar, carbon fiber, other like materials, or combinations thereof, may also be utilized. A memory effect can be described as a material that can be manipulated from a first position to a second position and then return to the first position upon release from the second position.

The connection node(s) 310 can provide a connection point for the expandable member(s) 312. The connection node(s) 310 may be constructed, formed, or manufactured utilizing a material such as, but not limited to, plastics, silicon, metal, metal alloys, synthetic materials, polymers, absorbable polymers, Teflon, Mylar, carbon fiber, other like materials, or combinations thereof. In one example, the connection node(s) 310 can be constructed, formed, and/or manufactured with the expandable member(s) 312. In alternative examples, the connection node(s) 310 may be connected to, or affixed to the expandable member(s) 312 through an adhesive, fastener, glue, connector, cement, epoxy, binder, or other adhesive or fastening methods or device, or combinations thereof.

The magnetic node(s) 311 can provide a connection point for the expandable member(s) 312. The magnetic node(s) 311 may be constructed, formed, or manufactured utilizing a material such as, but not limited to, plastics, silicon, metal, metal alloys, synthetic materials, polymers, absorbable polymers, Teflon, Mylar, carbon fiber, other like materials, or combinations thereof that are impregnated or infused with magnetic materials and/or elements. In at least one example, the magnetic node(s) 311 can be constructed, formed, and/or manufactured with the expandable member(s) 312. In alternative examples, the magnetic node(s) 311 may be connected to, or affixed to the expandable member(s) 312 through an adhesive, fastener, glue, connector, cement, epoxy, binder, or other adhesive or fastening methods or device, or combinations thereof.

In at least one version, the magnetic stent 300A and/or stent body 302 can be protected, compressed, and/or contained by a sheath, cover, or transportation device 332. The sheath, cover, or transportation device 332 can be coupled to a needle 334 or other device capable of allowing the sheath, cover, or transportation device 332 to be removed from a vessel and/or tissue.

Figure 3B:
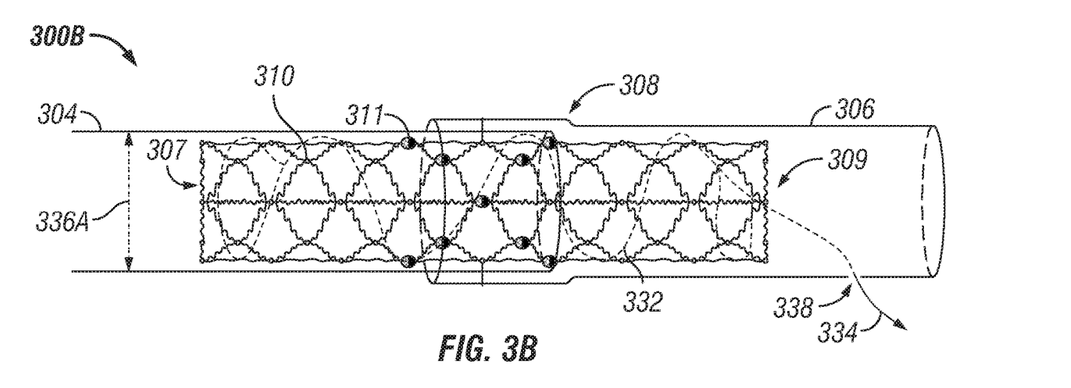
FIG. 3B is an illustration of a magnetic stent, donor and recipient vessels.

FIG. 3B is an illustration of a magnetic stent 300B, a donor vessel 304 and a recipient vessel 306. The magnetic stent 300B can have a stent body 302 that defines the hollow structure or hollow tubular body (not illustrated) that allows for a fluidic transfer, such as, but not limited to a blood flow 330, from a first opening 307 of the magnetic stent 300B to a second opening 309 of the magnetic stent 300B. In at least one version, the magnetic stent 300B includes a magnetic expansion region 308 that can expand, contract, and/or compress based on the activation and/or deactivation of a magnetic field around and/or through the magnetic expansion region 308. The magnetic stent 300B and/or stent body 302 can also include other expandable region(s) and/or section(s). The magnetic stent 300B and/or stent body 302, in at least one version, include connection node(s) 310, magnetic node(s) 311, and expandable member(s) 312. The nodes 310/311 and expandable member(s) 312 in combination with the magnetic expansion region can provide for the expansion, and/or compression of the magnetic stent 300B and/or stent body 302 and a change of diameter of the magnetic stent 300B and/or stent body 302 from a first diameter 336A to a second diameter illustrated FIG. 3C.

A sheath, cover, or transportation device 332 can be removed from surrounding, containing, and/or compressing the magnetic stent 300B and/or stent body 302. In at least one version, the sheath, cover, or transportation device 332 is coupled to a needle 334 or other removal device. In other versions, the sheath, cover, or transportation device 332 and needle 334 are constructed, manufactured, and/or formed from the same material. The needle 334 can create or pass through an opening 338. The opening 338 can created in any number of vessels and/or tissues to allow for the removal of the sheath, cover, or transportation device 332.

Figure 3C:
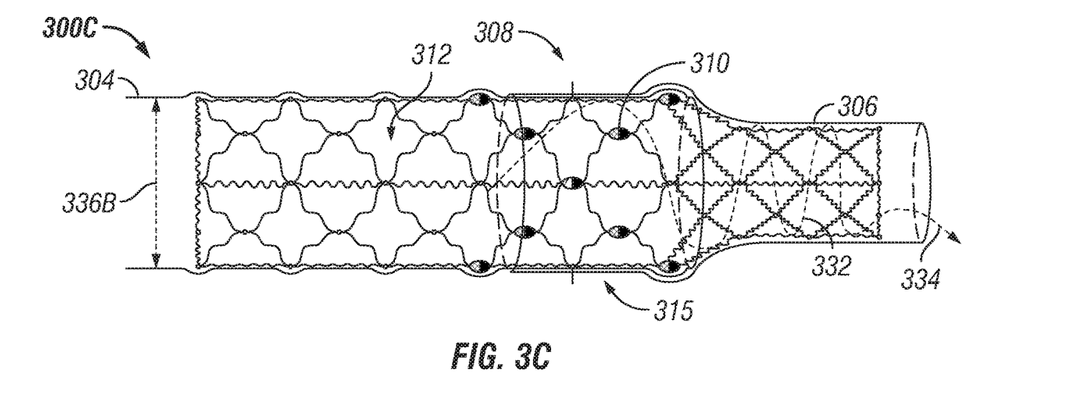
FIG. 3C is an illustration of an expanded magnetic stent, donor and recipient vessels.

FIG. 3C is an illustration of an expanded magnetic stent 300C, a donor vessel 304, and a recipient vessel 306. The magnetic stent 300C can have a stent body 302 that defines the hollow structure or hollow tubular body (not illustrated) that allows for a fluidic transfer, such as, but not limited to a blood flow 330, from a first opening of the magnetic stent 300C to a second opening of the magnetic stent 300C.

The connection node(s) 310, magnetic node(s) 311, and expandable member(s) 312 can work in combination, and with an expansion cover (not illustrated) to expand, contain, and/or compress the magnetic stent 300C and/or stent body 302. As the magnetic stent 300C and/or stent body 302 is expanded, contained, and/or compressed a second inner diameter 336B can be the result. The sheath, cover, or transportation device 332 can also assist in the expansion, compression, and/or containment of the magnetic stent 300C and/or stent body 302.

The magnetic stent 300C and/or stent body 302 can be modified from a first inner diameter illustrated in FIG. 3B to a second inner diameter 336B to allow for a securing of the magnetic stent 300C and/or stent body 302 within the donor and recipient vessels 304/306. The securing can be through anchor(s) 315, and/or interaction with vessels and/or tissue. The anchor(s) can be an anchor point, atraumatic anchor or anchor point, and/or traumatic anchor or anchor point, where a traumatic anchor can puncture or be invasive to a vessel or tissue but would be an acceptable level of injury and/or be minimally invasive to secure the stent in place within the vessel or tissue. The anchor(s) can also be expandable, and/or maintained in a fixed position. In at least one example, the anchor(s) can extend radially from the circumference or outer surface of the magnetic stent 300C and/or stent body 302.

Figure 4A:
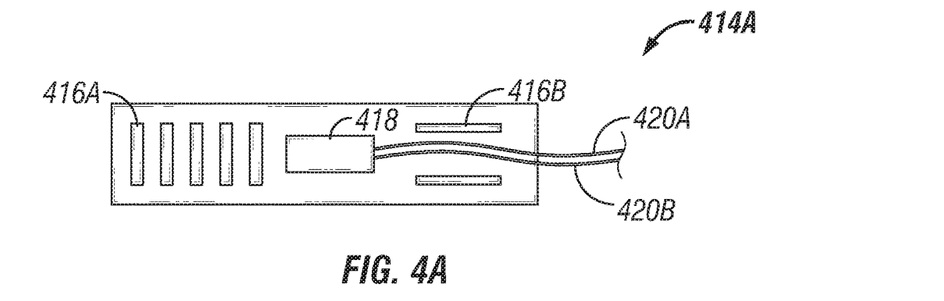
FIG. 4A is an illustration of an alternative expansion cover.

FIG. 4A is an illustration of an alternative expansion cover 414A. The expansion cover 414A may also include a magnetic material 416A and/or 416B. The magnetic material 416 (collectively) may be placed in specific location to generate specific expansions, and/or expansion zones for a stent (not illustrated). A sensor 418 can be coupled to wires 420A/420B to allow for a measurement and/or activation signal for the magnetic materials, and/or blood flow, and other measurements.

Figure 4B:
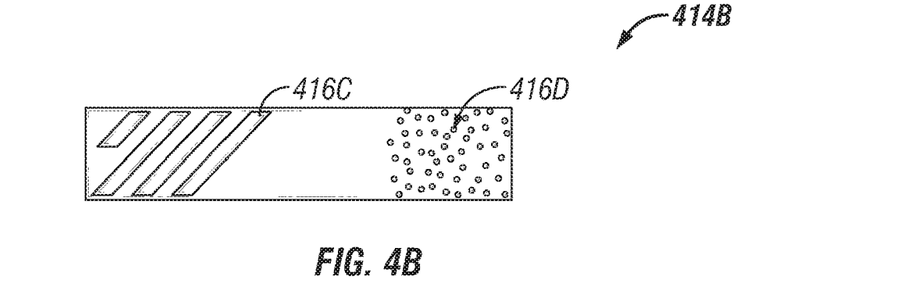
FIG. 4B is an illustration of an alternative expansion cover.

FIG. 4B an illustration of an alternative expansion cover 414B. The expansion cover 414A may also include a magnetic material 416C and/or 416D. The magnetic material 416 (collectively) may be placed in specific location to generate specific expansions, and/or expansion zones for a stent (not illustrated).

Figure 5A:
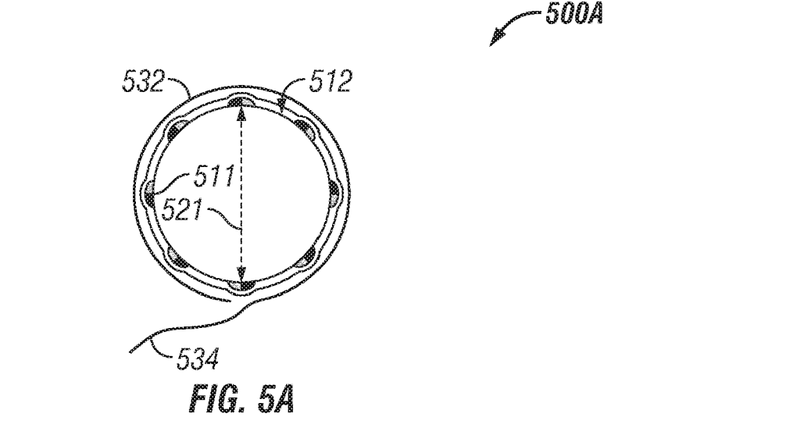
FIG. 5A is an illustration of a magnetic stent in a longitudinal or end view.

FIG. 5A is an illustration of a magnetic stent 500A in a longitudinal or end view. The magnetic stent 500A can include multiple magnetic node(s) 511 that can assist in the expansion, compress, and/or containment of the magnetic stent 500A and/or stent body (not illustrated). The magnetic node(s) 511 can be interconnected with expandable member(s) 512. In at least one example, the expandable member(s) 512 can be constructed, manufactured, and/or formed with magnetic materials and/or elements. These magnetic materials and/or elements can include, but are not limited to ferromagnetic materials such as iron nickel, and/or cobalt, alloys, and/or other rare earth metals or minerals. The expansion, compression, and/or containment of the magnetic stent 500A can also be assisted by a sheath, cover, or transportation device 532. The sheath, cover, or transportation device 532 can be constructed, manufactured, and/or formed with materials that prevent the expansion of the expandable member(s) 512, and/or the magnetic node(s) 511, while remaining flexible enough to be removed and/or perforated to ease removal. A needle 534 may also be coupled to the sheath, cover, or transportation device 532 to assist in the removal of the sheath, cover, or transportation device 532 through vessel(s) and/or tissue. The inner diameter 521 of the magnetic stent 500A can be modified by the expansion, compression, and/or containment of the magnetic stent 500A. In at least one version, a magnetic field can be utilized to collapse the magnet stent 500A, around a vessel or stent.

Figure 5B:
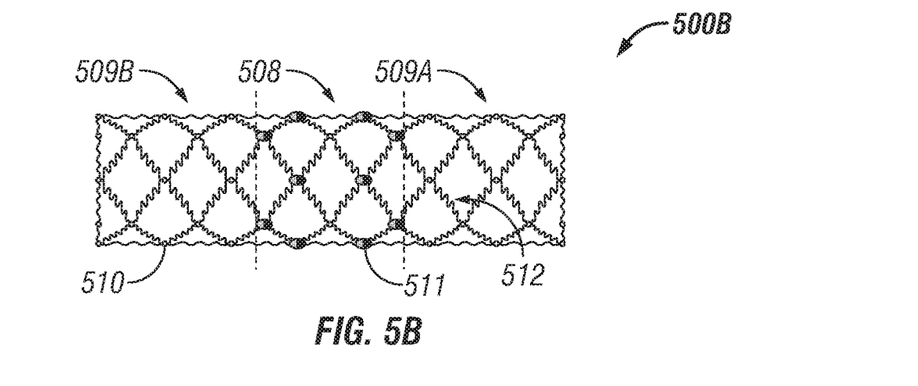
FIG. 5B is an illustration of a magnetic stent in a side view.

FIG. 5B is an illustration of a magnetic stent 500B in a side view. The magnetic stent 500B can have multiple regions, such as, but not limited to, a magnetic expansion region 508, expandable region 509A, and/or expandable region 509B. These regions 508/509A/509B can be expanded, compressed, and/or contained simultaneously and/or individually. The expansion can be triggered by interactions and/or caused by forces acting on the connection node(s) 510, magnetic node(s) 510, and/or expandable member(s) 512 such as, but not limited to a magnetic, electrical and/or electromagnetic force. In at least one example, a magnetic field (not illustrated) can be utilized to modify magnetic expansion region 508 via the magnetic node(s) 511. In other examples, the expandable member(s) 512 and/or connection node(s) 510 can be activated by fields, sensors, and/or monitors, or based on effects caused by a blood flow or fluid flowing through the magnetic stent 500B.

Figure 6:
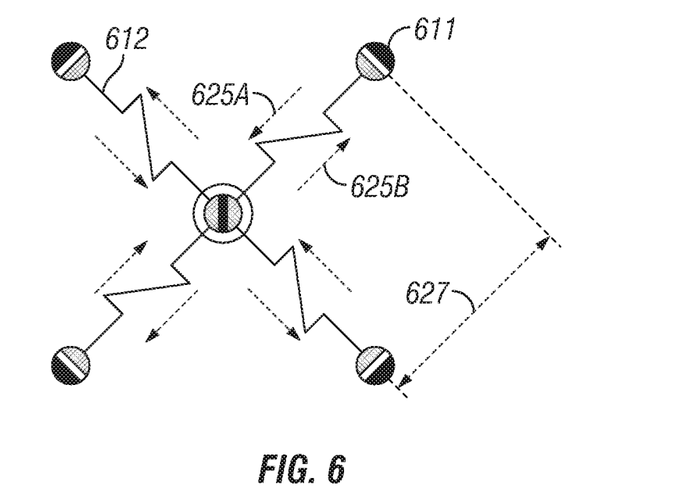
FIG. 6 is an illustration of a magnetic expansion structure.

FIG. 6 is an illustration of a magnetic node(s) 611 and expandable member(s) 612. The magnetic node(s) 611 can interact with each other individually and/or collectively to trigger or cause an expansion, compression, and/or containment of the expandable member(s) 612. In at least one example, a magnetic field can be generated by an external device or force that can cause the magnetic node(s) 611 to interact, modify, and/or move in response to magnetic field. The interaction, modification, and/or movement can cause the magnetic node(s) 611 to move and/or modify the expandable member(s) 612. For example, a magnetic field could cause the magnetic node(s) 611 to have an attractive force 625A that compresses and/or contains the expandable member(s) at a specific length 627. In other examples, a repulsive force 625B can cause an expansion of the expandable member to a specific length. These forces can also cause other magnetic node(s) 611, connection node(s) (not illustrated) and/or expandable member(s) 612 to also expand, compress, and/or be contained or constrained to specific level or positions.

Figure 7A:
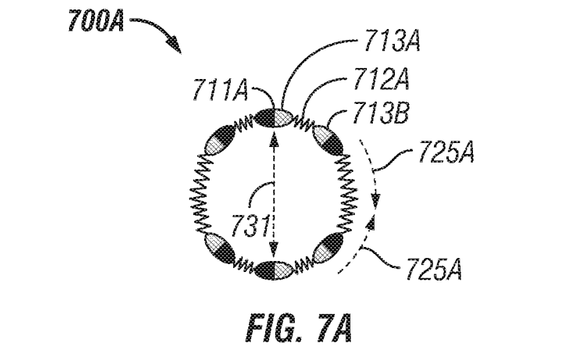
FIG. 7A is an illustration of a magnetic stent in an unexpanded state in a longitudinal or end view.

FIG. 7A is an illustration of a magnetic stent 700A in an unexpanded state in a longitudinal or end view. The magnetic stent 700A can be expanded, compressed, and/or contained by a magnetic field, sheath, cover, and/or transport device (not illustrated). In at least one version, the magnetic stent 700A includes magnetic node(s) 711, and expandable members 712. The magnetic stent 700A can also include connection node(s) (not illustrated) and/or non-expandable member(s) (not illustrated). The expandable member(s) 712 can allow for the expansion, compression, and/or containment of the magnetic stent.

For example, when the expandable member(s) 712 are in an unexpanded state the magnetic stent 700A can have a first internal radius 731 that in at least one version can be increased. In other versions, the first internal radius can be decreased. The increase/decrease in the radius of the magnetic stent 700A can be caused by an attractive force and/or a repulsive force (not illustrated). The forces can be caused by the poles of magnetic node(s) 711. For example, when the north magnet pole of a first magnetic node is pointed at the south magnet pole of a second magnetic node an attractive force can cause the expandable member to compress between the two magnetic nodes. The length, diameter, and/or size of the magnetic stent 700A can also be modified by the attractive force.

Figure 7B:
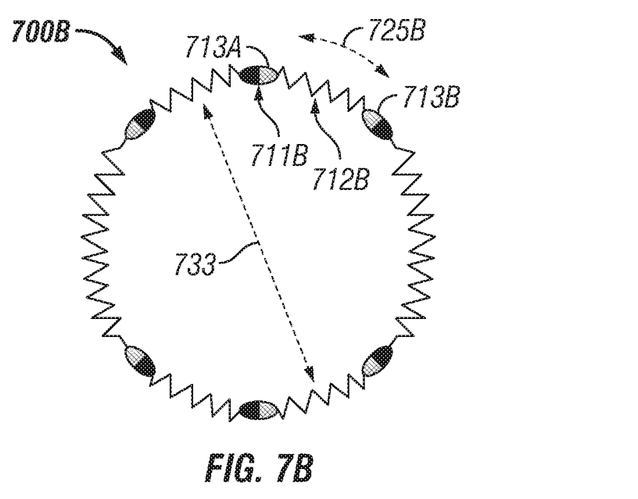
FIG. 7B is an illustration of a magnetic stent in an expanded state in a longitudinal or end view.

FIG. 7B is an illustration of a magnetic stent 700B in an expanded state in a longitudinal or end view. The magnetic stent 700B can be expanded, compressed, and/or contained by a magnetic field, sheath, cover, and/or transport device (not illustrated). In at least one version, the magnetic stent 700B includes magnetic node(s) 711, and expandable members 712. The magnetic stent 700B can also include connection node(s) (not illustrated) and/or non-expandable member(s) (not illustrated). The expandable member(s) 712 can allow for the expansion, compression, and/or containment of the magnetic stent 700B.

For example, when the expandable member(s) 712 are in an expanded state the magnetic stent 700B can have a second internal radius that in at least one version can be decreased. In other versions, the second internal radius can be further increased. The increase/decrease in the radius of the magnetic stent 700B can be caused by an attractive force (not illustrated) and/or a repulsive force. The forces can be caused by the poles of magnetic node(s) 711. For example, when the north magnet pole of a first magnetic node is pointed at the north magnet pole of a second magnetic node a repulsive force can cause the expandable member to expand between the two magnetic nodes. In another example, the expandable member(s) 712 can be manufactured with magnetic materials or elements that can be attracted and/or repulsed by the magnetic node(s) 711 and/or a magnetic field (not illustrated). In yet another example, the magnetic node(s) 711 can have their magnetic strength modified by sensor(s), monitor(s), and/or a fluid flow through the magnetic stent 700B.

Figure 8:
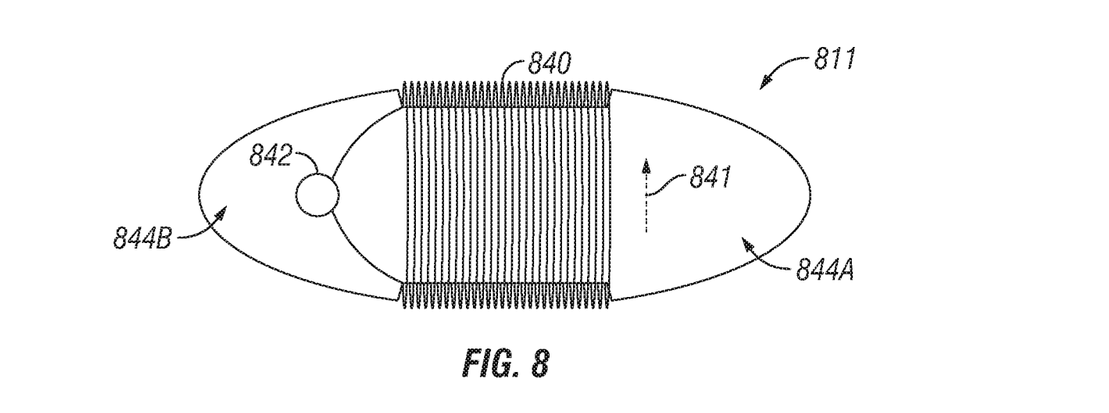
FIG. 8 is an illustration of a magnetic connection node.

FIG. 8 is an illustration of a magnetic node 811. The magnetic node 811 in at least one version, can be created, constructed, and/or manufactured with magnetic materials, elements, and/or electromagnetic windings. A winding 840 can be utilized to create the coil surrounding a core for an electromagnet for the magnetic node 811. In at least one example, the core would be ferromagnetic metal such as iron or ferrimagnetic compounds. In other examples, the core could include steel, laminated silicon steel, laminated cores and/or sheets, silicon alloys, other allows, vitreous metals, powdered metals such as iron, carbonyl iron, hydrogen-reduced iron, molypermalloy, nickle-iron, sendust, KoolMU, nanocrystalline, and/or ferrites and/or air. The winding 840 can be utilized with an electrical connection 842 to provide a voltage and/or current to the winding 840 that initiates a corresponding magnetic field. In at least one example, the electrical filed or energies may come from the natural fields or energy of the human body. The voltage and/or current applied to the winding 840 can cause a first magnetic pole 844A and a second magnetic pole 844B to be created. In at least one example, the first magnetic pole 844A is a north magnetic pole and the second magnetic poly 844B is a south magnetic pole. In other examples, the voltage and/or current polarity is reversed and the magnetic field is also reversed casing the first magnetic pole 844A to be a south magnetic pole and the second magnetic pole 844B is a north magnetic pole.

Figure 9:
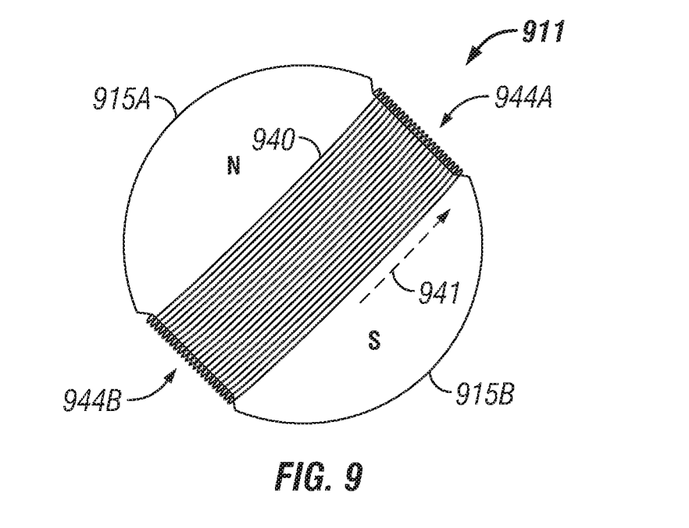
FIG. 9 is an illustration of a magnetic connection node.

FIG. 9 is an illustration of a magnetic node 911. The magnetic node 911 in at least one version, can be created, constructed, and/or manufactured with magnetic materials, elements, and/or electromagnetic windings. A winding 940 can be utilized to create the coil for an electromagnet for the magnetic node 911. The winding 940 when utilized with an electrical connection (not illustrated) that can provide a voltage and/or current to the winding 940 to generate the corresponding magnetic field. The voltage and/or current applied to the winding 940 cause a north magnetic pole 944A and a south magnetic pole 944B to be created. In at least one example, a current flows in a first direction 941 through the winding 940 creating the north magnetic pole, and the south magnetic pole. In other examples, the voltage and/or current polarity can be reversed and the corresponding magnetic field reversed causing the north magnetic pole to become a south magnetic pole, and the south magnetic pole to become a north magnetic pole.

Figure 10:
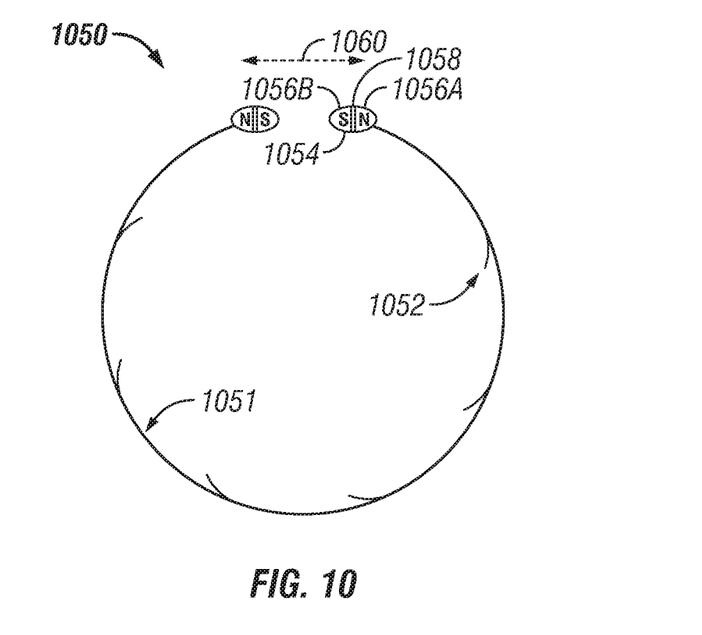
FIG. 10 is an illustration of a magnetic stent.

FIG. 10 is an illustration of a magnetic stent 1050. In at least one version, the magnetic stent 1050 can have at least one anchor 1052 along the inner circumference 1051 of the magnetic stent 1050. In other versions, the anchor(s) 1052 can also be placed along the outer circumference of the magnetic sent 1050. A first magnetic node 1054A can interact with a second magnetic node 1054B to expand, contract, compress, and/or contain the magnetic stent 1050. The magnetic nodes 1054A/1054B can each have a north magnetic pole 1056A, and a south magnetic pole 1056B that are separated by a winding 1058. Based on the polarity of the magnetic poles 1056A/1056B a force 1060 is created that attracts or repulses the magnetic nodes 1054A/1054B from one another, and opening or closing the magnetic stent 1050. For example, the magnetic stent 1050 can be utilized for a surgery that requires the stent to seal the outer surface of a vessel and/or portion of tissue. In other examples, the magnetic stent 1050 is utilized for heart operations to open a vessel and/or portion of tissue to increase the blood flow through and/or to a specific region.

Figure 11A:
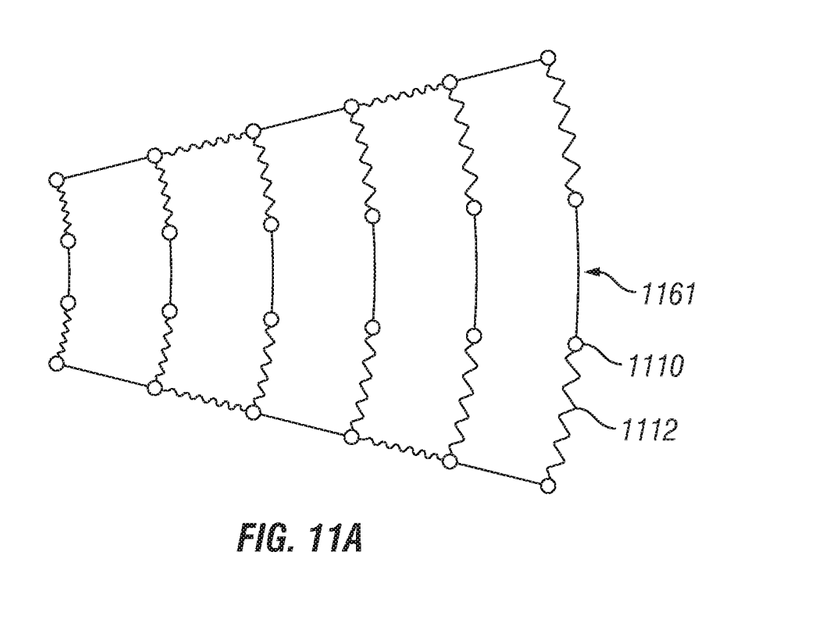
FIG. 11A is an illustration of an expandable magnetic structure for a magnetic stent in a side view.

FIG. 11A is an illustration of an expandable magnetic structure for a magnetic stent in a side view. A magnetic stent (not illustrated) can include connection node(s) 1110, magnetic node(s) 1111, expandable member(s) 1112, and/or non-expandable members 1161. The members 1112/1161 can be constructed and/or manufactured of varying lengths and thicknesses. With varying lengths, the expandable member(s) 1112 can allow a stent to be configured for any number of cross-sections, expansions, compressions, and/or profiles. A combination of connection node(s) 1110, and non-expandable member(s) also assist in creating any number of cross-sections, and/or profiles for a stent. In at least one example, the non-expandable members may also be structural member(s).

Figure 11B:
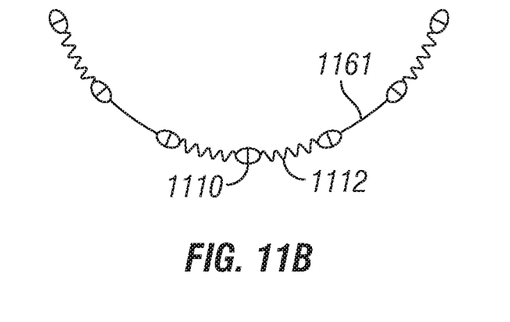
FIG. 11B is an illustration of an expandable magnetic structure for a magnetic stent in a longitudinal or end view.

FIG. 11B is an illustration of an expandable magnetic structure for a magnetic stent in a partial longitudinal or end view. A magnetic stent (not illustrated) can include connection node(s) 1110, magnetic node(s) 1111, expandable member(s) 1112, and/or non-expandable members 1161. The members 1112/1161 can be constructed and/or manufactured of varying lengths and thicknesses. With varying lengths, the expandable member(s) 1112 can allow a stent to be configured for any number of cross-sections, and/or profiles. A combination of connection node(s) 1110, and non-expandable member(s) also assist in creating any number of cross-sections, and/or profiles for a stent. In at least one example, an anchor or set of anchor(s) may also be coupled to the connection node(s) 1110, magnetic node(s) 1111, expandable member(s) 1112, and/or non-expandable member(s).

Figure 12A:
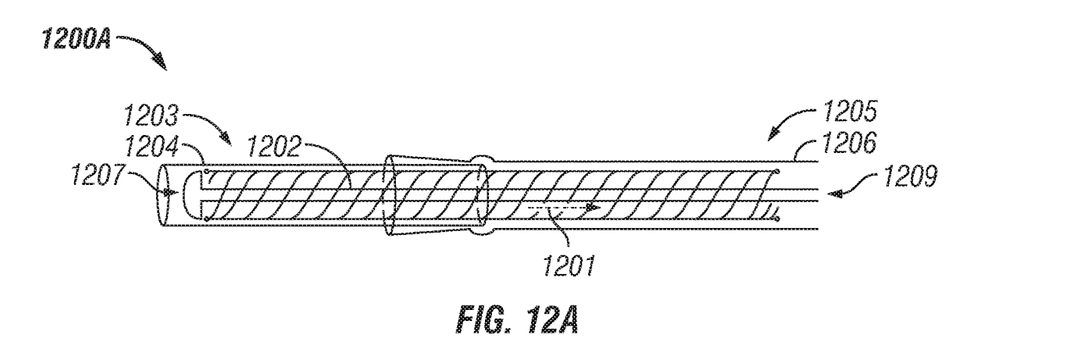
FIG. 12A is an illustration of a magnetic stent in an unexpanded state.

FIG. 12A is an illustration of a magnetic stent 1200A in an unexpanded state. The magnetic stent 1200A includes a stent body 1202 that can define a hollow tubular structure with a first opening at a proximal end of the stent body 1202 and/or hollow tubular structure and a second opening at a distal end of the stent body 1202 and/or hollow tubular structure. A donor vessel 1204, and/or recipient vessel 1206 can surround, and/or be contained by a magnetic stent 1200A.

Figure 12B:
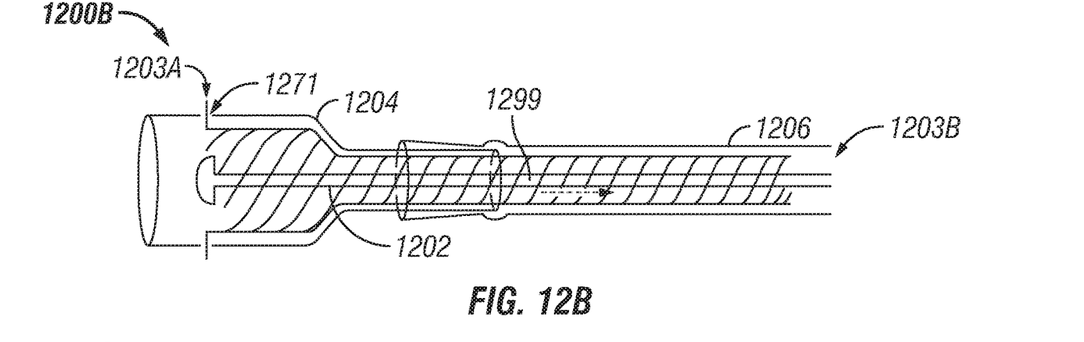
FIG. 12B is an illustration of a magnetic stent in a partially expanded state.

FIG. 12B is an illustration of a magnetic stent 1200B in a partially expanded state. The magnetic stent 1200B can include anchor(s) 1203A at the proximal end and anchor(s) 1203B at the distal end, and/or along the outer surface of the magnetic stent 1200B. The anchor(s) 1203A/1203B can interface with the inner and/or outer surface of a vessel, such as, but not limited to, a donor vessel 1204, recipient vessel 1206, or other tissue to secure the magnetic stent 1200B in place. A stent delivery tool 1299 may also allow for the insertion and/or placement of the magnetic stent 1200B. In at least one example, the stent delivery tool 1299 may also include magnetic properties that allow for the expansion and/or activation of the expansion based on the positional relationship of the stent delivery tool 1299 and/or the magnetic stent 1200B.

For example, the magnetic stent 1200B may be constructed of expandable and/or non-expandable structures, such as, but not limited to member(s) and/or connection node(s) infused, impregnated or including magnetic materials or elements. The magnetic materials or elements allow the magnetic stent to expand, compress, or contain a vessel or tissue to a specified diameter, profile, and/or cross-section. The magnetic stent 1200B may be expanded, compressed, and/or contained in individual sections or regions, or as a single stent, or in a combination of sections or regions.

Figure 12C:
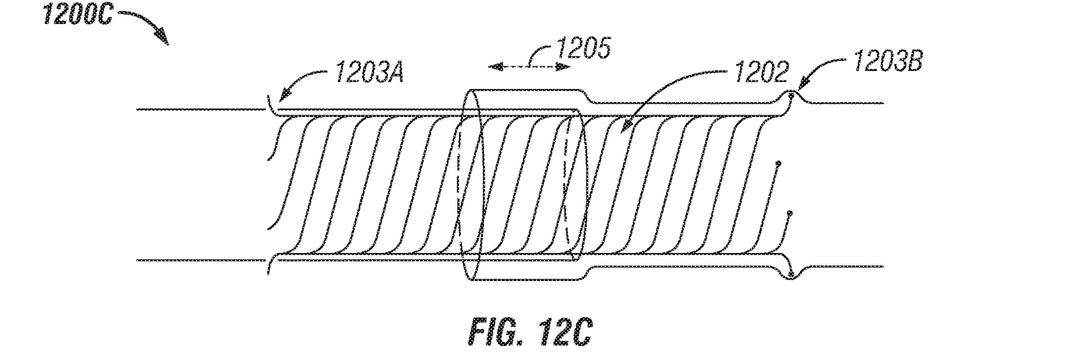
FIG. 12C is an illustration of a magnetic stent in a fully expanded state.

FIG. 12C is an illustration of a magnetic stent 1200C in a fully expanded state. When the magnetic stent 1200C is in a fully expanded state, it can allow for an increased state of blood flow or other fluids through the stent body 1202. In at least one example, the magnetic stent 1200C includes anchor(s) 1203A, and 1203B that can be atraumatic or traumatic anchors. The anchor(s) 1203A/1203B can be expandable or transferable, and/or held in a fixed position. The anchor(s) 1203A can interface and/or couple to a vessel and/or tissue at an interface point 1271. Similarly, anchor(s) 1203B can interface and/or couple to a vessel and/or tissue at an interface point.

Figure 13:
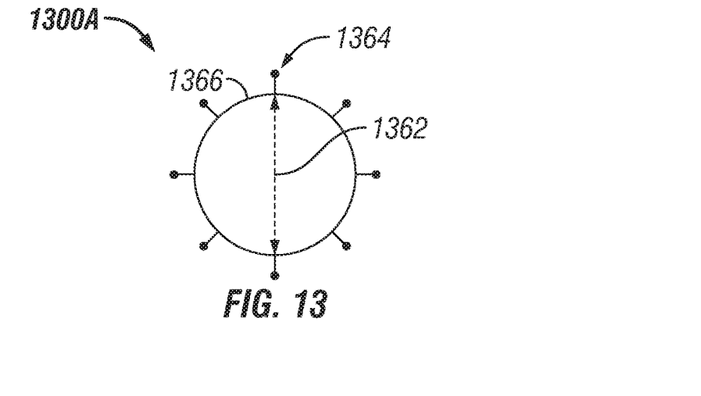
FIG. 13 is an illustration of a magnetic stent in a fully expanded state.

FIG. 13 is an illustration of a magnetic stent 1300 in a fully expanded state. The magnetic stent 1300 in a fully expanded state can have an inner diameter 1362 that in at least one version can be reduced. The outer surface 1366 of the magnetic stent 1300 can include a smooth outer surface, a textured surface, and/or anchor(s) 1364 coupled to the outer surface 1366. The anchor(s) 1364 can be atraumatic and/or traumatic. In at least one version, the anchor(s) 1364 extend radially from the outer surface 1366, and at either end of the magnetic stent 1300. In other versions, the anchor(s) 1364 may be placed along the length of the magnetic stent 1300, in equally spaced position, or unequally spaced positions.

While this disclosure has been particularly shown and described with reference to preferred embodiments, it will be understood by those skilled in the art that various changes in form and detail may be made therein without departing from the spirit and scope of the invention. The inventors expect skilled artisans to employ such variations as appropriate, and the inventors intend the invention to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

While various embodiments in accordance with the principles disclosed herein have been described above, it should be understood that they have been presented by way of example only, and not limitation. Thus, the breadth and scope of this disclosure should not be limited by any of the above-described exemplary embodiments, but should be defined only in accordance with any claims and their equivalents issuing from this disclosure. Furthermore, the above advantages and features are provided in described embodiments, but shall not limit the application of such issued claims to processes and structures accomplishing any or all of the above advantages.

Additionally, the section headings herein are provided for consistency with the suggestions under 37 C.F.R. 1.77 or otherwise to provide organizational cues. These headings shall not limit or characterize the invention(s) set out in any claims that may issue from this disclosure. Specifically, and by way of example, although the headings refer to a "Technical Field," the claims should not be limited by the language chosen under this heading to describe the so-called field. Further, a description of a technology as background information is not to be construed as an admission that certain technology is prior art to any embodiment(s) in this disclosure. Neither is the "Brief Summary" to be considered as a characterization of the embodiment(s) set forth in issued claims. Furthermore, any reference in this disclosure to "invention" in the singular should not be used to argue that there is only a single point of novelty in this disclosure. Multiple embodiments may be set forth according to the limitations of the multiple claims issuing from this disclosure, and such claims accordingly define the embodiment(s), and their equivalents, that are protected thereby. In all instances, the scope of such claims shall be considered on their own merits in light of this disclosure, but should not be constrained by the headings set forth herein.

I claim:

1. A stent apparatus for use in surgical applications, comprising:
    a hollow tubular section with a proximal end for engaging with a first vessel and a distal end for engaging with a second vessel allowing the first vessel and the second vessel to be fluidly coupled together through end-to-end anastomoses;
    at least one anchor point connected to the hollow tubular section for engaging with at least one of the first vessel and the second vessel;
    wherein the hollow tubular section is comprised of at least one modifiable member; and
    wherein the hollow tubular section is comprised of at least one magnetic connection node coupled to the at least one modifiable member and the at least one magnetic connection node causes a modification of the at least one modifiable member to engage the at least one modifiable member with at least one of the first vessel and the second vessel.

2. The stent apparatus of claim 1, wherein the proximal end has at least one atraumatic anchor point.

3. The stent apparatus of claim 1, wherein the proximal end has at least one traumatic anchor point.

4. The stent apparatus of claim 1, wherein the distal end has at least one atraumatic anchor point.

5. The stent apparatus of claim 1, wherein the distal end has at least one traumatic anchor point.

6. The stent apparatus of claim 1, wherein the at least one modifiable member comprises a material that is modifiable by a magnetic field.

7. The stent apparatus of claim 1, wherein the at least one modifiable member has expansion memory.

8. The stent apparatus of claim 1, wherein the at least one modifiable member is connected to form a circumference of the proximal end.

9. The stent apparatus of claim 1, wherein the at least one modifiable member is connected to form a circumference of the distal end.

10. The stent apparatus of claim 1, wherein the at least one modifiable member is connected to form a circumference of the hollow tubular section.

11. The stent apparatus of claim 1, wherein the hollow tubular section is further comprised of at least one structural member.

12. The stent apparatus of claim 11, wherein the at least one structural member is connected to the at least on modifiable member by the at least one magnetic connection node.

13. The stent apparatus of claim 11, wherein the hollow tubular section is further comprised of at least one connection node.

14. The stent apparatus of claim 13, wherein the at least one modifiable member is connected by the at least one magnetic connection node, and the at least one connection node.

15. The stent apparatus of claim 1, wherein the hollow tubular section further comprises at least one atraumatic anchor extending radially from the hollow tubular section.

16. The stent apparatus of claim 1, wherein the hollow tubular section further comprises at least one traumatic anchor extending radially from the hollow tubular section.

17. The stent apparatus of claim 1, wherein the hollow tubular section further comprises at least one sensor.

18. The stent apparatus of claim 17, wherein the at least one sensor is a blood flow sensor.

19. The stent apparatus of claim 1, wherein the stent apparatus further comprises a stent wrapping.

20. A system for stent delivery in surgical applications, comprising:
    a stent delivery tool for inserting a stent into a vessel, the stent delivery comprising:
    wherein the stent comprises a hollow tubular section with a proximal end for engaging with a first vessel and a distal end for engaging with a second vessel allowing the first vessel and the second vessel to be fluidly coupled together through end-to-end anastomoses;
    at least one anchor point connected to the hollow tubular section for engaging with at least one of the first vessel and the second vessel;
    wherein the hollow tubular section is comprised of at least one modifiable member; and
    wherein the hollow tubular section is comprised of at least one magnetic connection node coupled to the at least one modifiable member and the at least one magnetic connection node causes a modification of the at least one modifiable member to engage the at least one modifiable member with at least one of the first vessel and the second vessel.

* * * * *